(12) United States Patent
Reisberg et al.

(10) Patent No.: US 7,122,006 B2
(45) Date of Patent: Oct. 17, 2006

(54) MANAGEMENT, CARE AND TREATMENT OF ALZHEIMER'S DISEASE AND RELATED DEMENTIAS

(76) Inventors: Barry Reisberg, 20 Waterside Plz., #7K, New York, NY (US) 10010; Stefanie R. Auer, Traunreiter Weg 10, Sulbach 102 Bad Ischl 4820 (AT)

( * ) Notice: Subject to any disclaimer, the term of this patent is extended or adjusted under 35 U.S.C. 154(b) by 0 days.

(21) Appl. No.: 10/632,558

(22) Filed: Jul. 31, 2003

(65) Prior Publication Data

US 2005/0070766 A1    Mar. 31, 2005

Related U.S. Application Data

(60) Provisional application No. 60/399,908, filed on Jul. 31, 2002.

(51) Int. Cl.
*A61B 5/00*    (2006.01)

(52) U.S. Cl. ........................................ 600/300; 128/920

(58) Field of Classification Search ........ 600/300–301, 600/544–546, 558, 559, 582, 595; 128/905, 128/920; 434/236–238, 262
See application file for complete search history.

(56) References Cited

U.S. PATENT DOCUMENTS

| | | | | |
|---|---|---|---|---|
| 5,082,446 A | * | 1/1992 | Sclan et al. | 434/236 |
| 5,150,716 A | * | 9/1992 | Franssen et al. | 600/587 |
| 5,782,777 A | * | 7/1998 | Souren-Franssen et al. | 600/587 |
| 6,067,986 A | * | 5/2000 | Kluger et al. | 600/595 |

* cited by examiner

*Primary Examiner*—Max F. Hindenburg
*Assistant Examiner*—Michael C Astorino
(74) *Attorney, Agent, or Firm*—Gottlieb, Rackman & Reisman, P.C.

(57) ABSTRACT

A method is provided for the care and treatment of AD and related dementias by staging patients using the FAST, BCRS, and/or the GDS staging elements, translation of the staging elements into corresponding developmental ages (DAs), using the patient DA to determine the overall management and care needs of patients with AD and related retrogenic dementias, refining these needs based upon axioms refined by postulates and caveats.

5 Claims, No Drawings

MANAGEMENT, CARE AND TREATMENT OF ALZHEIMER'S DISEASE AND RELATED DEMENTIAS

This application claims priority of provisional patent application 60/399,908, filed Jul. 31, 2002.

FIELD OF THE INVENTION

The invention relates to Alzheimer's disease (AD) and related dementia management and care.

BACKGROUND OF THE INVENTION

Retrogenesis is the biologic process by which normal physiologic, psychologic, and behavioral processes in the course of dementia reverse those of normal human developmental acquisition. Relationships between normal human development and dementia have long been recognized. For example, the ancient Greek playwright Aristophanes noted in 423 B.C. that "old men are children twice over". Similarly, the English dictionary defines dotage, a synonym for dementia and related conditions, as "childishness of old age". Physicians and scientists have also recognized similarities between senile dementia and normal early human development. For example, in the first American textbook of psychiatry, Benjamin Rush (1793), noted that in old age the body shows the marks not only of a second childhood but even the marks of second infancy. In the twentieth century investigators began to find relationships between Piagetian developmental stages and degeneration occurring in dementing disorders.

In 1982 Dr. Reisberg and associates published the Global Deterioration Scale, which described seven major stages of normal aging and the progressive dementia of AD. Later, in work published from 1984 to 1986, Dr. Reisberg identified the characteristic progression of functional changes in normal aging and progressive AD. Sixteen successive functional stages were described. It was immediately recognized by Dr. Reisberg that this functional progression in aging and AD reversed the stages of functional acquisition in normal human development. Subsequent work by Dr. Reisberg and his colleagues also indicated that the pattern of loss of feeding capacities and figure drawing abilities in AD reversed the normal acquisition pattern in early human development. Together with Dr. Emile Franssen, Dr. Reisberg found that: (1) normal infantile neurological reflexes emerge in the course of AD, and (2) that these reflexes occur at the same point in AD, from the perspective of the inverse functional stage, as would be anticipated from the human developmental model. This discovery of a method for diagnosis of incontinence of corticocerebral origin by neurologic examination has been previously described in U.S. Pat. No. 5,826,585 awarded to Dr. E. H. Franssen and Dr. B. Reisberg.

In other work by Dr. Reisberg and his associates it was found that childhood and infant psychological test measures are useful in assessing residual cognitive capacities in, what was previously termed "untestable", severe AD. These findings are described in U.S. Pat. No. 5,082,446 awarded in 1992 to Dr. S. G. Sclan and Dr. B. Reisberg. Work by other investigators, indicated that a widely used dementia assessment, the Mini Mental State Examination, showed just as robust relationships between the mental age of children, as has been observed for the relationship between Mini Mental State Examination scores and any independent objective, non-cognitive assessments in AD patients.

On the basis of the findings described above, as well as other findings, it was concluded in 1998 that the stages of AD can be usefully described in terms of corresponding developmental ages (DAs) (Reisberg, et al., J Neural Transm,[Suppl] 54: 9–20, 1998). We noted that the management needs of AD patients and many of the behavioral changes in these patients could be explained by the DA model.

Later, in 1999, we concluded that the process by which the progressive changes in AD and related dementing disorders reverses the order of acquisition in normal human development should be given a new and appropriate name. Therefore, we termed this process, "retrogenesis" (Reisberg, et al., International Psychogeriatrics, 11: 7–23, 1999 and Reisberg, et al., Eur Arch Psychiatry Clin Neurosci 249: Suppl. 3, 28–36, 1999). We hypothesized that an entire science of management for AD and related dementing disorders could be formulated based upon an understanding of this retrogenesis process. We also hypothesized at that time that this understanding would have to incorporate both similarities and differences between AD and normal human development.

BRIEF DESCRIPTION OF THE PRESENT INVENTION

The present invention provides a broad methodology for a science of management, care and treatment of AD and related dementias. This science is based on: (1) axioms, (2) postulates, and (3) caveats. The proper interaction of these elements results in the new science of management, and in new discoveries regarding the methods for caring for AD and related dementia patients such as the discoveries described herein.

AD is the major form of dementing disorder. AD is the paradigmatic retrogenic illness process, with many features more or less precisely reversing those of normal human developmental acquisition. Interestingly, in AD this developmental reversal applies to a certain extent even to the temporal course of loss of capacities versus the temporal course of acquisition the same capacities in normal human development. However, other dementing disorders may follow this retrogenic course to a greater or lesser extent, depending upon the pathophysiologic basis of the dementia.

The methodology for the new science of management, care and treatment is based upon the phenomenon of retrogenesis. Employing this science involves: (1) staging of the magnitude of the dementia using a procedure which can be retrogenically translated into the developmental age of the dementia patient, (2) recognizing the relevance of appropriate axioms, i.e., universal human needs and desires, applicable at all ages, (3) recognizing the relevant retrogenic postulates, and (4) recognizing the relevant caveats, i.e. exceptions to the DA/retrogenesis model based upon the nature of human aging and AD and related dementias.

By recognizing these features, i.e the developmental age, universal axioms, retrogenic postulates, and appropriate caveats, the care of AD patients, and patients with related dementing processes, can be optimized. Specifically, patient satisfaction and capacity can be optimized and suffering can be minimized and/or, eliminated.

DETAILED DESCRIPTION OF A PREFERRED EMBODIMENT

In accord with the present invention, measures were developed whereby patients with AD and related dementias could be properly assessed in terms of the corresponding developmental age. These measures are the Functional Assessment Staging procedure (FAST) (Reisberg, 1988), and, measures which in large series of subjects with AD which is uncomplicated by other disease processes, are optimally concordant with the FAST staging procedure. These latter, optimally concordant measures are known as the Brief Cognitive Rating Scale (BCRS) and the Global Deterioration Scale (GDS) (Reisberg, et al. 1982, 1983a, 1983b, 1986, 1990, 1993).

To determine the developmental age of the AD patient or a patient with a related retrogenic dementia, one may first stage a dementia patient using the FAST staging procedure. Each of the FAST stages in AD and related retrogenic dementias are directly translatable into corresponding developmental ages (DAs) based upon the point in normal development when the FAST stage capacity is acquired (see table 1). For example, FAST stage 5, the loss of ability to select clothing properly in the context of dementia, corresponds to a DA of 5–7 years, the point in normal development when this capacity is acquired. Therefore, the DA corresponding to FAST stage 5 is 5–7 years. It should be noted that the FAST staging procedure is an ordinal (hierarchical) measure, and therefore, the staging with the FAST must be done using the entire scale and not simply a single functional element.

In dementia, there are cognitive changes as well as functional changes, just as in normal development, there is acquisition of cognitive capacities, as well as functional capacities. Therefore, a complete DA assessment of a dementia patient must take into consideration the cognitive capacity of the patient as well as the functional capacity. This is accomplished using the optimally concordant cognitive and related assessments from the BCRS and/or the global assessments from the GDS.

Specifically, if a patient scores a 5 on a BCRS axis, or a 5 on the GDS, this corresponds to a DA of 5–7 years, just as a score of 5 on the FAST corresponds to a DA of 5–7 years. The DA for any single BCRS axis or the GDS is calculated on the basis of the DA identified by the corresponding FAST score. For example, to calculate, the cognitive DA, one can add BCRS axis 1-4 scores, divide the total by 4, which results in a mean cognitive score which can be translated into a cognitive DA. For example, a BCRS axis 1-4 mean score of 5.0, is optimally concordant with and corresponds to a FAST stage 5, with a corresponding DA of 5–7 years.

One can use the GDS score to give a global DA. This GDS score is also optimally concordant with and corresponds to a FAST score which can be used to calculate the dementia patient's DA. For example, a GDS score of 5 is optimally concordant with and corresponds to a FAST stage score of 5. Therefore, the DA of a dementia patient with a GDS score of 5 is 5–7 years.

A complete DA incorporates the FAST score and a BCRS axis 1-4 mean score, or a FAST score and a GDS score, or a FAST score, BCRS axis 1-4 mean score, and a GDS score. The complete dementia patient DA is arrived at by first calculating the stage, as the (FAST stage)+(the mean BCRS stage 1-4 score), equals a total which is divided by 2. This resultant stage is translated into the stage based DA. Alternatively, the complete dementia patient DA may be arrived at by first calculating the stage as the (FAST stage)+(the GDS stage), equals in total which is divided by 2. The resultant stage is translated into the stage based DA.

A finer description of the DA takes into consideration the DA differences in accordance with the individual values calculated from the FAST, each of the BCRS axes, and the GDS.

The DA is used to determine the care science using the methodology described herein.

First, axioms are taken into consideration. "Axioms" in this context are self-evident basic human needs and desires, applicable at all ages.

Axiom I: All human beings avoid trauma and humiliation. AD patients, and patients with related retrogenic dementias at any stage avoid, or rebel against, experiences which are perceived as humiliating. The most prominent humiliating experience for the AD and related retrogenic dementia patient is appearing "stupid". Therefore, even early in the disease process, patients may avoid being questioned. As the disease progresses, patients may resist the humiliation of requiring a caregiver. So called "delusions", such as that people are stealing things, have a psychologic basis in that AD and related dementia patients at these stages would prefer to accuse others of taking things, rather than accept the humiliation of admitting to themselves or others that they cannot remember.

Axiom II: All human beings seek a sense of accomplishment. In early AD and related dementias (GDS stage 4), this sense of accomplishment can come from continued productivity. For example, an artist may continue to paint. A lawyer may continue the pretense of working on case. One judge had his daughter write opinions. Stage 5 patients may continue to insist that they are working, even if they have been forced to retire. Later in AD and related dementias, a sense of accomplishment may come from folding towels, and other simple, DA appropriate activities.

This axiom has important corollaries (consequences or results which follow from the axiom). These are that:
(1) all human beings resist losses.
(2) a sense of accomplishment can be fostered, by beginning with what an AD and related dementia patient can do and building upon this, and
(3) a sense of accomplishment comes from practicing an area of residual expertise or learning new things.

Axiom III: All human beings seek a sense of dignity and self-worth. This may come from practicing previously mastered skills. It may also come from optimal participation in "adult" activities. It may also be fostered by introducing necessary caregivers as "friends." A corollary of this is that if an AD or related dementia patient perceives an activity as "infantile" or "childish", and therefore as an affront to their dignity, then they may become angry and refuse to participate.

Axiom IV: All human beings are social organisms. Therefore, the social needs of the AD and related dementia patient remain throughout the illness process. Even in the late stage (stage 7), patients continue to require interaction with caregivers and others for mental and physical health and well being.

Axiom V: All human beings seek praise and acceptance. As social organisms, AD and related dementia patients continue to require positive social reinforcement throughout the course of the illness process in order to maintain their motivation and skills.

Axiom VI: All human beings have the capacity to learn. One aspect of this is that AD and related dementia patients can be retrained in many of the skills which they have lost by breaking the tasks down into small stages which are achievable, and praising the patient for their accomplishments.

Axiom VII: All human beings require love. This is necessary for the emotional and physical health of the AD and related dementia patient at all points in the illness processes.

Axiom VIII: All human beings have the capacity for happiness, if basic needs are fulfilled. This means that AD and related retrogenic dementias are physiologically congruent processes. As such, if proper care is provided and social, emotional, and other needs are met, then AD and other dementia patients need not suffer and they can derive satisfaction from their existence.

Axiom IX: All human beings have the need for physical movement. Indeed, movement is sometimes said to be a fundamental feature of animal life. As is the case of the other axioms, this fundamental need is frequently ignored or not recognized in AD and other dementia patients to such an extent that, until recently, dementia patients were routinely restrained towards the goal of preventing falling. Naturally, this restraint actually increased falls in patients who were made increasingly unstable from the restraints. The need for movement remains frequently unrecognized in the dementia patient.

Axiom X: All human beings have the capacity to remember. As is true of many of the other axioms, this basic human capacity is frequently not recognized particularly in the late stage (stage 7) AD and related retrogenic dementia patient. If the AD patient's memory is placed in the context of the DA of the AD patient, their memory capacity becomes comprehensible and assessable. Just as a one year old child will forget people and events more quickly, a stage 7 patient will forget people and events more quickly than an adult. Three weeks is a very long time for a stage 7 AD patient or a 1 year old child. Just as is true of all humans at all ages, emotional memories are particularly strong in AD and related retrogenic dementias.

Axiom XI: All human beings have the capacity to think. As with other basic human capacities, this capacity is sometimes not recognized in the AD and related retrogenic dementia patient with deleterious consequences. For example, caregivers may sometimes speak unflatteringly about the late stage 6 and early stage 7 AD patient, thinking that because the patient cannot articulate, they do not understand. The patient may become agitated in response to the caregiver's unempathetic comments. Unfortunately, the caregiver, not recognizing the patient's comprehension, may think the agitation is sporadic and arbitrary, rather than a response to their crude and critical remarks.

Axiom XII: All human beings seek to influence their environment. This basic human need and desire is also frequently underestimated in the stage 7 AD and related retrogenic dementia patient. For example, although a stage 7 AD patient's babbling may be uninterpretable to the caregiver, the patient seeks to make their desire known and many become agitated, or violent, if not "listened to".

Axiom XIII: All human beings have a sense of "taste", i.e., likes and dislikes. Just as an infant will throw away a toy which they do not like, an AD patient or a patient with a related retrogenic dementia has preferences which are expressed and are interpretable at any stage. These preferences are sometimes not recognized. For example, a case manager recommended "any ID bracelet" for an early stage 6 AD patient because "she won't notice." In actuality, this patient would be highly insulted by an unattractive plastic bracelet and this patient maintained a sense of style and beauty.

It should be noted that although the axioms are applicable at all ages, the manner of application of the axioms at each stage of the disease is dependent upon the DA of the AD and related retrogenic dementia patient. For example, for Axiom 1, although all human beings avoid trauma and humiliation, the manner of avoidance is very different for a stage 4 patient with early AD from the manner of avoidance of a stage 7 AD patient with severe AD. The differences are dependant upon the DA, i.e., the avoidance of trauma and humiliation in the stage 4 AD patient has many elements of similar phenomena in an 8–12 year old child, and the avoidance of trauma and humiliation in the stage 7 AD patient has many elements of similar phenomena in an infant.

Postulates are testable hypotheses of AD and related retrogenic dementia patient care.

The postulates are based upon the retrogenesis observations and the DA model of the stages of AD and related retrogenic dementias, reviewed in the preceding sections. The validity of the postulates is subject to scientific investigation. A summary of some of the major postulates follows.

Postulate I: The magnitude of care and supervision required by an AD or related retrogenic dementia patient at a DA, is mirrored by the amount of care and supervision required by a child or infant at the corresponding DA. For example, an AD patient at stage 7, corresponding to an infancy DA, requires approximately the same amount of care and supervision as an infant, etc.

Postulate II: The kinds of activities enjoyed by an AD or related retrogenic dementia patient at a particular DA, are mirrored by the kinds of activities enjoyed by children at a corresponding DA. For example, just as child of 2 to 5 years may enjoy working on puzzles, drawing with crayons, assisting with simple household chores, etc., similar activities are appropriate for the stage 6 AD patient at a corresponding DA.

Corollaries of postulate II include the following:
(1) The kinds of activities which children find frightening or upsetting at a D.A. are mirrored by the kinds of activities AD or related retrogenic dementia patients find upsetting at a corresponding DA.
(2) The kinds of activities which a child considers "childish" or "baby like", at a particular DA, are mirrored by the kinds of activities an AD or related retrogenic dementia patient may find humiliating.
(3) The kinds of activities which promote healthy and optimal motoric development in children, are similarly the kinds of activities which minimize motoric degeneration in AD and related retrogenic dementias.

Postulate III: The capacity of an AD or related retrogenic dementia patient to perform in an area of residual expertise is dependent upon the DA. If a child at the corresponding DA can master the task, then an AD patient at the DA can potentially retain the residual capacity. Variability in AD and related retrogenic dementia patients' loss of capacity is mirrored by a corresponding variability in children's ability to master the task. Therefore, expectations must be in accord with the DA of the AD patient. A corollary of this postulate is that as an AD patient approaches loss of capacity, they develop anticipatory anxieties. For example, AD patients commonly develop anxieties regarding toileting in FAST stage 6c, prior to loss of urinary continence in FAST stage 6d. Similarly, some patients develop anxieties about completing their income tax in stage 4.

Postulate IV: Previous experiences may determine the kinds of activities enjoyed by an AD or related retrogenic dementia patient. For example, one GDS stage 6, FAST stage 6d AD patient was very anxious about having her front yard clean. Naturally, an urban patient might not be interested in cleaning a yard.

Postulate V: The emotional level of the AD or related retrogenic dementia patient is dependent on the DA. For example, just as a 2 to 3 year old child may become "cranky" at various points in the day, a stage 6d AD patient at a corresponding DA may develop "mood swings".

Postulates VI: Life experiences appropriate to the DA become most relevant for AD and related retrogenic dementia patients at any particular stage. For example, a man's only interest may have been his work. However, at stage 5 (DA: 5 to 7 years), much of the interest in his previous job (e.g. business, medicine, etc.), is lost. At this point, DA appropriate activities can be introduced.

Postulate VII: Socialization of the AD and related retrogenic dementia patient is dependent upon the DA. For example, just as an infant of a year or less, does not yet relate socially with other infants, a stage 7 AD patient does not relate or socialize with other stage 7 patients.

Postulate VIII: Diversity in children's and infant's activities and interests is mirrored in diversity in AD and related retrogenic dementia patients' interests and activities at a corresponding DA. A corollary of this is that just as all normal, healthy, children at a given age clearly can be shown to have much in common, despite acknowledged diversity, all "uncomplicated" AD patients at a given stage have much in common, despite acknowledged diversity. For example, all normal, healthy, one year old children have much in common with each other in comparison with normal, healthy, 12 year old children. Conversely, all stage 7a uncomplicated AD patients have much in common, as compared to all uncomplicated stage 4 AD patients.

Postulate IX: The emotional changes which occur in AD and related retrogenic dementias at a DA are mirrored by the emotional changes observed in children at a corresponding DA. This is similar to postulate V, but concerns specifics. For example, delusions occur in AD patients which are very similar to childhood fantasies, at the corresponding DAs.

Postulate X: Care settings appropriate to AD and related retrogenic dementia patients at a DA are mirrored by care settings appropriate to children at the corresponding DA. A corollary of this postulate is that just as institutions would be considered an inappropriate and undesirable care setting for infants and toddlers, institutions are inappropriate settings for the care of stage 7 and stage 6 AD patients. Therefore, resources currently devoted to nursing home care should probably be shifted to care in community residences.

The analogy of nurseries and schools for children to day-care centers for AD and related retrogenic dementia patients also applies in this regard.

Postulate XI: Vulnerability (emotional, physical, and cognitive) of the AD and related retrogenic dementia patient at a DA, is mirrored by the vulnerability of children and infants at the corresponding DA. For example, just as an infant is vulnerable to social deprivation, poor care, and physical insult, a stage 7 AD patient is vulnerable to social deprivation, poor care, and physical insult. The result of these social, emotional and physical injuries is excess disability.

Postulate XII: The need of an AD and related retrogenic dementia patient for physical movement is mirrored by the corresponding DA. A young child requires more than simply walks and/or, running back and forth, for optimal physical growth and attainment. Motoric development in children is also dependent upon the child dressing, developing eating skills, ball playing, etc. The same kinds of skills are required by the AD and related retrogenic dementia patient to prevent precipitous physical decline.

Postulate XIII: Just as one judges development in an infant or child by what the infant or child can do and has achieved, not by what the infant and child cannot do, the AD and related retrogenic dementia patient at any particular DA should be assessed in terms of their residual skills and accomplishments, what they have learned and relearned, not by what they cannot do.

Postulate XIV: The developmental analogy is sufficiently strong to trigger DA appropriate childhood memories, beliefs, and anxieties in the AD and related retrogenic dementia patient. For example, most FAST stage 6e AD patients will state that their parents are alive. These DA appropriate memories are the basis of the statement, incorporated in the Blessed, et al., Dementia Scale, that AD patients tend to dwell in the past.

Postulate XV: The language changes of the AD and related retrogenic dementia patient are mirrored by the DA. For example, when speech abilities break down in the AD patient at FAST stage 6e, patients commonly develop verbigeration and neologisms, which are very similar to the babbling of infants as they acquire speech at an equivalent DA.

Caveats are exceptions to the DA-retrogenesis model, based on the nature of human aging and AD and related retrogenic dementias. Caveats which modify the retrogenic/DA model of AD make the care and management of the AD and related retrogenic dementia patient a complex art as well as a science. Some of the major caveats are enumerated below.

Caveat I: Development in infants and children is accompanied by increasing expectations, whereas AD and related retrogenic dementias at all stages are accompanied by progressively diminished expectations. These contrasting phenomena are accompanied by widely divergent social consequences. For example, the tendency, societally, is to praise children and to become frustrated with AD patients. However growth, within the context of an individual's capacity for growth, is dependent upon praise for one's accomplishments.

Caveat II: AD and related retrogenic dementia patients experience developmentally analogous brain changes, however they do not undergo, developmentally analogous physical changes. Therefore AD and related retrogenic dementia patients are physically larger and more formidably appearing than children. Furthermore, until stage 7, AD and related retrogenic dementia patients have the physical habits of a normal adult. These physical features produce special consequences for AD and other retrogenic dementia patients in comparison with children. For example, the AD patient's normal appearance conveys a level of sagacity and competence which is not assumed to be present in children at the same DA.

Also, because of the absence of a physical retrogenesis, the physical capacities of AD and related retrogenic dementia patients may sometimes exceed those of DA comparable children and infants. For example, a very well cared for stage 7b patient, who receives retraining, can be relatively dexterous compared to a one year old. For example, one 7b patient was able to lace, button, and slip on clothing.

Another consequence of the AD and related retrogenic dementia patient's size and strength in comparison with their DA peers, is that a grasp reflex in a stage 7 dementia patient can be much stronger and more difficult to release then an infant's grasp reflex, with consequences for the management of the dementia patient.

Caveat III: AD and related retrogenic dementia patients can, to some extent, draw upon previously mastered skills, whereas infants and children may not have access to these skills. Consequently, AD and related retrogenic dementia patients may be relatively skilled and "precocious" in comparison with their chronologically younger DA peers. For example, even in late stage 7, long after serviceable speech has been lost, AD patients may occasionally, e.g., during their sleep, or in response to startle or pain, utter seemingly forgotten words. Infants do not have access to such words.

Caveat IV: AD and related retrogenic dementia patients can, to some extent, draw upon previously mastered knowledge, whereas infants and children may not have access to this knowledge. For example, a FAST 7d AD patient who always had an immaculate household uttered "aagh", when a caregiver dropped shoes in the middle of the floor. This same 7d AD patient would "whack" a caregiver who put their elbows on the table.

Caveat V: AD and related retrogenic dementia patients are older than their DA peers and old age predisposes to various physical disabilities which influence the life and experience of a dementia patient. For example, cataracts predispose AD patients to visual hallucinations, etc.

Caveat VI: AD and related retrogenic dementia patients appear to be more prone to rigidity than their DA peers. The causes probably include the dementia patient's brain disease in the absence of physical involution and the relative immobility of dementia patients. The rigidity can greatly increase disability in the AD patient, ultimately resulting in contractures.

Caveat VII: AD and related retrogenic dementia patients can potentially concentrate on a task longer than infants or children at a corresponding DA. Conversely, infants and children are more distractable and impatient than AD and related retrogenic dementia patients. For example, one 7c, AD patient is known to stare at a newspaper for perhaps an hour. An 11 month old infant will look at a book for a few minutes.

Caveat VIII: AD and related retrogenic dementia patients appear to be less fascinated by the world and less inquisitive than infants and children at a corresponding DA. For example, a 2 year old child may continuously ask questions such as "what is this?", an AD patient at stage 6e is not inquisitive in this manner.

Therefore, a care science in AD and related retrogenic dementias can be firmly grounded in universal human, retrogenic and dementia specific principles. The ingredients for the quality care recipe are described above in detail. These principles can potentially impact positively on the quality of life and excess disability of AD and other retrogenic dementia patients at this juncture. Potentially, much of the suffering and distress associated with AD and other retrogenic dementias can be relieved.

Further to this invention this new methodology results in new care concepts which are novel but are also consequential from the discoveries described above. These new concepts include the use of infant and child care personnel for the care and management of AD and related retrogenic dementia patients at corresponding DAs. Another discovery resulting from this work is of the utility of large type reading materials for AD and related retrogenic dementia patients at DAs at which children would ordinarily use large type reading materials. More broadly, activities for AD and related retrogenic dementia patients should be provided which are DA appropriate and management in general of AD and related retrogenic dementia patients should be DA appropriate.

Clinical Advantages of the Invention

The invention has accomplished the following:

1. It provides a methodology for translating the cognitive, functional and other behavioral changes in dementia patients into DAs.
2. The DAs can provide a guide for the management and care needs of AD patients and patients with related retrogenic dementias.
3. These management and care needs are further refined by taking into consideration universal human needs and desires, applicable at all ages, but better understood on the basis of the DA, known as axioms. The specific axioms are a subject of this invention.
4. The management and care needs are further refined by taking into consideration postulates based upon the DA model. The specific postulates are a subject of this invention.
5. The management and care needs are further refined by taking into consideration caveats, which are exceptions to the DA-retrogenesis model based on the nature of human aging and AD and related retrogenic dementias. The specific caveats are a subject of this invention.
6. The findings from the methodology described in 1-4 above result in novel care discoveries. These novel discoveries include the use of infant and child care personnel for the care and management of AD and related retrogenic dementia patients at corresponding DAs. These novel discoveries also include the use and the utility of large type reading materials for AD patients at DAs at which children would ordinarily use large type reading materials. More broadly, these novel discoveries include the provision of activities for AD and related retrogenic dementia patients which are DA appropriate and provision of general management services in AD patients and patients with related retrogenic dementias which are DA appropriate.
7. The procedures described in points 1-6 above, are further refined by taking into consideration precise DA capacities of AD and related retrogenic dementia patients, based upon individual DA capacities calculated from individual DA scores on the basis of patient specific FAST scores, patient specific individual BCRS Axis scores, and patient specific individual GDS scores.

We claim:

1. A method for care and treatment of Alzheimer's disease and related dementias comprising
   (a) staging of patients using the Functional Assessment Staging procedure, and/or the Brief Cognitive Rating Scale, and/or the Global Deterioration Scale;
   (b) translation of each of the Functional Assessment Staging procedure, Brief Cognitive Rating Scale and Global Deterioration Scale; staging elements into the corresponding developmental ages,
   (c) utilization of the patient developmental age to determine the overall management and care needs of patients with Alzheimer's disease and related retrogenic dementias;
   (d) refinement of these overall management and care needs based upon universal basic needs and desires termed axioms;
   (e) refinement of these overall management and care needs based upon the retrogenic observations and the developmental age model of the stages of Alzheimer's disease, based upon postulates chosen from the following:
  (i) the magnitude of the care and supervision required by an Alzheimer's disease or related retrogenic dementia patient at a developmental age, is mirrored by the amount of care and supervision required by a child or infant at the corresponding developmental age;
  (ii) the kind of activities enjoyed by an Alzheimer's disease or related retrogenic dementia patient at a particular developmental age are mirrored by the kind of activities enjoyed by children or infants at a corresponding developmental age;
  (iii) the capacity of an Alzheimer's disease or related retrogenic dementia patient to perform in an area of residual expertise is dependent upon the developmental age;
  (iv) previous experiences determine the activities enjoyed by an Alzheimer's disease or related retrogenic dementia patient;
  (v) the emotional level of the Alzheimer's disease or related retrogenic dementia patient is dependent upon the developmental age;
  (vi) life experiences appropriate to the developmental age become most relevant for Alzheimer's disease and related retrogenic dementia patients at any particular stage;
  (vii) socialization of the Alzheimer's disease and related retrogenic dementia patient is dependent upon the developmental age;
  (viii) diversity in children's and infant's activities and interests is mirrored in diversity in Alzheimer's disease and related retrogenic dementia patient's interests and activities at a corresponding developmental age;
  (ix) the emotional changes which occur in Alzheimer's disease and related retrogenic dementias at a developmental age are mirrored by the emotional changes observed in children at a corresponding developmental age;
  (x) care settings appropriate to Alzheimer's disease and related retrogenic dementia patients at a developmental age are mirrored by care settings appropriate to children at the corresponding developmental age;
  (xi) vulnerability of the Alzheimer's disease and related retrogenic dementia patient at a developmental age, is mirrored by the vulnerability of children at the corresponding developmental age;
  (xii) the need of an Alzheimer's disease AD and related retrogenic dementia patient for physical movement is mirrored by the corresponding developmental age;
  (xiii) just as one judges development in an infant or child by what the infant or child can do and has achieved, not by what the infant and child cannot do, the Alzheimer's disease and related retrogenic dementia patient at any particular developmental age should be assessed in terms of their residual skills and accomplishments, what they have learned and re-learned, not by what they cannot do;
  (xiv) the developmental analogy is sufficiently strong to trigger developmental age appropriate childhood memories, beliefs, and anxieties in the Alzheimer's disease and related retrogenic dementia patient;
  (xv) the language changes of the Alzheimer's disease and related retrogenic dementia patient are mirrored by the developmental age;
  (f) refinement of these overall management and care needs based upon caveats to the developmental age retrogenesis model, based on the nature of human aging and Alzheimer's disease and related retrogenic dementias selected from the group consisting of:
    i. development in infants and children is accompanied by increasing expectations, whereas Alzheimer's disease and related retrogenic dementias at all stages are accompanied by progressively diminished expectations;
    ii. Alzheimer's disease and related retrogenic dementia patients experience developmentally analogous brain changes, however, they do not undergo developmentally analogous physical changes;
    iii. Alzheimer's disease and related retrogenic dementia patients can, to some extent, draw upon previously mastered skills, whereas infants and children may not have access to these skills;
    iv. Alzheimer's disease and related retrogenic dementia patients can, to some extent, draw upon previously mastered knowledge, whereas infants and children may not have access to this knowledge;
    v. Alzheimer's disease and related retrogenic dementia patients are older than their developmental age peers and old age predisposes to various physical disabilities which influence the life and experience of a dementia patient;
    vi. Alzheimer's disease and related retrogenic dementia patients appear to be more prone to rigidity than their developmental age peers;
    vii. Alzheimer's disease and related retrogenic dementia patients can potentially concentrate on a task longer than infants or children at a corresponding developmental age;
    viii. Alzheimer's disease and related retrogenic dementia patients appear to be less fascinated by the world and less inquisitive than infants and children at a corresponding developmental age.

2. The method for care and treatment of Alzheimer's disease and related dementias of claim 1, wherein said axioms are selected from the group consisting of:
  all human beings avoid trauma and humiliation;
  all human beings seek a sense of accomplishment;
  all human beings seek a sense of dignity and self worth;
  all human beings are social organisms;
  all human beings seek praise and acceptances;
  all human beings have the capacity to learn;
  all human beings require love;
  all human beings have the capacity for happiness;
  all human beings have the need for physical movement;
  all human beings have the capacity to remember;
  all human beings have the capacity to think;
  all human beings seek to influence their environment; and
  all human beings have a sense of personal preference.

3. The method for care and treatment of Alzheimer's disease and related dementias of claim 1 wherein postulate (ii) has corollaries including the following:
  (a) the activities which children find frightening or upsetting at a developmental age are mirrored by the activities Alzheimer's disease and related retrogenic dementia patients find upsetting at a corresponding developmental age;
  (b) the activities which are childish or baby like to a child, at a particular developmental age, are mirrored by the activities an Alzheimer's disease or related retrogenic dementia patient may find humiliating;

(c) the activities which promote healthy and optimal motoric development in children, are similarly the activities which minimize motoric degeneration in Alzheimer's disease and related retrogenic dementia patients.

4. The method for care and treatment of Alzheimer's disease of claim 1, wherein the translation of staging elements into corresponding developmental ages is accomplished by the following steps:
   (a) the Functional Assessment Staging procedure stages are converted into corresponding developmental age based upon the point in normal development when the Functional Assessment Staging procedure functional elements are acquired;
   (b) the actual patient Functional Assessment Staging procedure, Brief Cognitive Rating Scale, and Global Deterioration Scale; scores which were developed in an optimally concordant manner with the progression of dementia in Alzheimer's disease, are converted into developmental ages based upon actual scores, using the developmental age model which was developed from the Functional Assessment Staging procedure based conversions;
   (c) a cognitive developmental age can be calculated from Brief Cognitive Rating Scale Axis 1-4 total scores divided by 4;
   (d) general patient developmental ages can be calculated by adding the cognitive developmental age to the functional developmental age and dividing the sum by 2 or adding the Global Deterioration Scale; score to the Functional Assessment Staging procedure score and dividing the sum by 2;
   (e) individual patient developmental ages can be further refined for therapeutic purposes by utilization of individual developmental age based Functional Assessment Staging procedure, Brief Cognitive Rating Scale Axis and Functional Assessment Staging procedure scores.

5. The method for care and treatment of Alzheimer's disease and related dementias of claim 1, further comprising the steps of
   (a) using infant and child care personnel for the care and management of Alzheimer's disease and related retrogenic dementia patients at corresponding developmental ages, and
   (b) utilizing large type reading materials for Alzheimer's disease and related retrogenic dementia patients at developmental ages at which children would ordinarily use large type reading materials.

* * * * *